United States Patent [19]

Yoshioka

[11] Patent Number: 4,882,434

[45] Date of Patent: Nov. 21, 1989

[54] GAMMA-LACTONECARBOXYLIC ACID DERIVATIVES AND THEIR USE AS ANTIBACTERIAL AGENTS OR INTERMEDIATES

[75] Inventor: Kouichi Yoshioka, Kyoto, Japan

[73] Assignee: Takeda Chemical Industries, Ltd., Osaka, Japan

[21] Appl. No.: 111,514

[22] Filed: Oct. 21, 1987

[30] Foreign Application Priority Data

Oct. 29, 1986 [JP] Japan ................................ 61-257629
Apr. 6, 1987 [JP] Japan ................................ 62-84477

[51] Int. Cl.$^4$ .................. C07D 405/12; C07D 409/12; C07D 413/14; C07D 417/12
[52] U.S. Cl. ...................................... 546/283; 549/60; 549/318
[58] Field of Search ................... 546/283; 549/316, 60

[56] References Cited

FOREIGN PATENT DOCUMENTS 0191989 8/1986 European Pat. Off. ............ 548/243
0219923 4/1987 European Pat. Off. ............ 514/370

Primary Examiner—Alan L. Rotman
Attorney, Agent, or Firm—Wenderoth, Lind & Ponack

[57] ABSTRACT

A compound represented by formula (I):

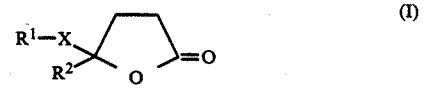

wherein
  $R^1$ is an organic residue through a carbon atom,
  $R^2$ is a carboxyl group which may be esterified or amidated, and
  X is an oxygen atom, or a sulfur atom which may be oxidized, or a salt thereof, which is useful as antibacterial agent or intermediate for synthesizing the same, and a process for preparing the same.

5 Claims, No Drawings

GAMMA-LACTONECARBOXYLIC ACID DERIVATIVES AND THEIR USE AS ANTIBACTERIAL AGENTS OR INTERMEDIATES

BACKGROUND OF THE INVENTION (a) Field of the Invention

The present invention relates to novel γ-lactonecarboxylic acid derivatives (2-substituted-5-oxo-2-tetrahydrofurancarboxylic acid derivatives) which are useful as antibacterial agents or intermediates for synthesizing the same, and to a process for preparing the derivatives.

(b) Description of the Prior Art

Recently, a novel antibiotic, TAN-588 (hereinafter sometimes referred to briefly as "TAN-588"), exhibiting antibacterial activity on gram-positive bacteria and gram-negative bacteria was discovered from new strains belonging to the genus Empedobacter and the genus Lysobacter isolated from soil (see Unexamined EPC Publication No. 0157544). Subsequently, it has been found that TAN-588 has a unique chemical structure represented by 2-[(4S)-4-acetamido-3-oxo-2-isoxazolidinyl]-5-oxo-2-tetrahydrofurancarboxylic acid.

The invention searches for novel TAN-588 derivatives having outstanding antibacterial activity and provides intermediates which are useful for preparing the derivatives.

We have conducted research on the synthesis of TAN-588 derivatives and found that novel 2-substituted-5oxo-2-tetrahydrofurancarboxylic acid derivatives include those having antibacterial activity and that these compounds can be useful intermediates for preparing TAN-588 derivatives. We have carried out further research and accomplished the present invention.

SUMMARY OF THE INVENTION

Thus, the present invention provides a compound represented by the formula (I):

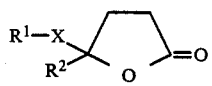
(I)

wherein $R^1$ is an organic residue through a carbon atom, $R^2$ is a carboxyl group which may be esterified or amidated, and X is an oxygen atom, or a sulfur atom which may be oxidized, or a salt thereof, and a process for preparing a γ-lactonecarboxylic acid derivative characterized in that a compound represented by the formula (II):

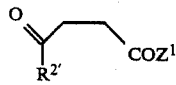
(II)

wherein $R^{2'}$ is an esterified carboxyl group, and $Z^1$ is a leaving group, and a compound represented by the formula (III):

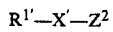
(III)

wherein $R^{1'}$ is an organic residue through a carbon atom, $X'$ is an oxygen atom or sulfur atom, and $Z^2$ is a leaving group, are subjected to a condensation reaction, and in that when desired, (i) $R^{1'}$ is converted to other organic residue $R^1$, (ii) the sulfur atom is treated with an oxidizing agent and thereby converted to an oxidized sulfur atom, or (iii) the esterified carboxyl group is hydrolyzed, amidated or subjected to a salt forming reaction and thereby converted to a carboxyl group or an amidated carboxyl group or a salt of carboxyl group, the process giving a compound represented by the formula (I):

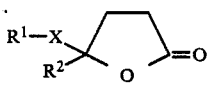
(I)

wherein $R^1$ is an organic residue through a carbon atom, $R^2$ is a carboxyl group which may be esterified or amidated, and X is an oxygen atom, or a sulfur atom which may be oxidized, or a salt thereof.

DESCRIPTION OF THE PREFERRED EMBODIMENT

Examples of organic residues through a carbon atom represented by $R^1$ and $R^{1'}$ are an alkyl which may be substituted, a cycloalkyl, an aryl which may be substituted and a heterocyclic group which may be substituted.

Examples of preferred alkyl groups are those having 1 to 6 carbon atoms such as methyl, ethyl, n-propyl, isopropyl, n-butyl, isobutyl, sec-butyl, tert-butyl, 1,1-dimethylpropyl, n-pentyl, isopentyl, n-hexyl, isohexyl and the like. Examples of substituents which may be possessed by such alkyl groups are halogens, cyano, alkoxyl, alkoxycarbonyl, acyl, acylamino, aryl, heterocyclic rings (pyridyl, thienyl, furyl, etc.) and the like.

Examples of useful cycloalkyl groups are $C_{4-6}$ cycloalkyl groups such as cyclobutyl, cyclopentyl and cyclohexyl.

Examples of useful aryl groups are phenyl, naphthyl and the like. Examples of substituents which may be possessed by such aryl groups are halogens, nitro, cyano, $C_{1-3}$ alkyl groups, $C_{1-3}$ alkoxyl groups and the like.

Examples of useful heterocyclic groups are 5- or 7-membered heterocyclic groups containing one sulfur, nitrogen or oxygen atom, 5- or 6-membered heterocyclic groups containing two to four nitrogen atoms, and 5- or 6-membered heterocyclic groups containing one or two nitrogen atoms and one sulfur or oxygen atom. Such a heterocyclic group may be present as condensed with a 6-membered cyclic group containing at least two nitrogen atoms or with a benzene ring.

More specific examples of useful heterocyclic groups are pyridyl, pyrimidinyl, pyrazinyl, pyridazinyl, pyranyl, imidazolyl, thiazolyl, isoxazolyl, pryrimidyl, naphthyridyl, tetrazolyl, triazolyl, furyl, benzothiazolyl and the like. Examples of subsituents which may be possessed by such heterocyclic groups are halogens, nitro, cyano, $C_{1-3}$ alkyl groups, $C_{1-3}$ alkoxyl groups and the like.

When $R^1$ and $R^{1'}$ is pyridyl or when the alkyl thereby represented has pyridyl as its substituents, the nitrogen atom of the pyridyl may be quaternized, preferably with $C_{1-3}$ alkyl (such as methyl, ethyl or propyl) which may have a substituent. Examples of useful substituents for the alkyl are phenyl which may have a substituent, carboxyl which may be esterified or amidated, cyano, hydroxyl and a cephem-3-yl represented by the formula

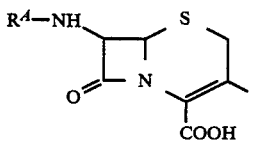

wherein $R^4$ is 2-thienylacetyl, phenylacetyl, 2-(2-amino-4-thiazolyl)-(Z)-2-methoxyiminoacetyl or like acyl.

Examples of counter anions for the quaternized pyridyl are external anions such as halogens, and intermolecular anions such as the carboxyl on the cepham ring or of $R^2$.

Examples of more preferred groups represented by $R^1$ and $R^{1'}$ are $C_{1-3}$ alkyl groups, phenyl which may be substituted with a halogen, and pyridyl (especially 2- or 4-pyridyl) which may be quaternized.

Examples of suitable esterified carboxyl groups represented by $R^2$ or $R^{2'}$ are those having as ester residues thereof alkyl having 1 to 10 carbon atoms, alkenyl, aryl, cycloalkyl, heterocyclic ring and silyl which may have a substituent. Examples of such esters are methyl ester, ethyl ester, n-propyl ester, isopropyl ester, tert-butyl ester, tert-amyl ester, benzyl ester, 4-bromobenzyl ester, 4-nitrobenzyl ester, 2-nitrobenzyl ester, 3,5-dinitrobenzyl ester, 4-methoxybenzyl ester, benzhydryl ester, phenacyl ester, 4-bromophenacyl ester, phenyl ester, 4-nitrophenyl ester, methoxymethyl ester, methoxyethoxymethyl ester, ethoxymethyl ester, benzyloxymethyl ester, acetoxymethyl ester, pivaloyloxymethyl ester, 2-methylsulfonylethyl ester, 2-trimethylsilylethyl ester, methylthiomethyl ester, trityl ester, 2,2,2-trichloroethyl ester, 2-iodoethyl ester, cyclohexyl ester, cyclopentyl ester, aryl ester, cinnamyl ester, 4-picolyl ester, 2-tetrahydropiranyl ester, 2-tetrahydrofuranyl ester, trimethylsilyl ester, tert-butyldimethylsilyl ester, tert-butyldiphenylsilyl ester, acetylmethyl ester, 4-nitrobenzoylmethyl ester, 4-methylbenzoylmethyl ester, phthalimidomethyl ester, propionyloxymethyl ester, 1,1-dimethylpropyl ester, 3-methyl-3-butenyl ester, succinimidomethyl ester, 3,5-di-tert-butyl-4-hydroxybenzyl ester, mesylmethyl ester, benzenesulfonylmethyl ester, phenylthiomethyl ester, iminomethylaminoethyl ester, 1-iminoethylaminoethyl ester, dimethylaminoethyl ester, pyridine-1-oxido-2-methyl ester, methylsulfinylmethyl ester, bis-(4-methoxyphenyl)methyl ester, 2-cyano-1,1-dimethylethyl ester, tert-butyloxycarbonylmethyl ester, benzoylaminomethyl ester, 1-acetoxyethyl ester, 1-isobutyryloxyethyl ester, 1-ethoxycarbonyloxyethyl ester, 1-cyclohexyloxycarbonyloxyethyl ester, phthalide ester(1,3-dihydro-3-oxo-1-isobenzofuranyl ester), 4-tert-butylbenzyl ester, 5-indanyl ester, 5-methyl-2-oxo-1,3-dioxolane-4-ylmethyl ester, 5-tert-butyl-2-oxo-1,3-dioxolane-4-ylmethyl ester and the like.

In some cases, these esters are used as carboxyl-protective groups. In such a case, tert-butyl esters, benzhydryl ester, and substituted or unsubstituted benzyl esters are suitable.

Examples of useful amidated carboxyl groups represented by $R^2$ or $R^{2'}$ are one or di-substituted alkyl amido, acylamido, 2-(4-carbonylamino-3-oxo-2-isoxazolidinyl)-5-oxo-2-tetrahydrofurancarboxylic acid represented by the formula:

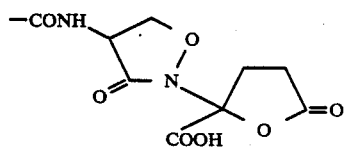

and salts or esters thereof. Examples of suitable esters are similar to those exemplified above.

Examples of halogens mentioned for the substituents are chlorine, bromine and fluorine.

Alkyl groups for such substituents are preferably those having 1 to 4 carbon atoms, such as methyl, ethyl, n-propyl, isopropyl, n-propyl and tert-butyl. Preferred alkoxyl groups for such substituents and those in alkoxycarbonyl groups therefore are groups having 1 to 4 carbon atoms, such as methoxy, ethoxy, n-butoxy and tert-butoxy. Preferred acyl groups for such substituents and those in acylamino groups therefore are groups having 1 to 4 carbon atoms, such as formyl, acetyl, propionyl and butyryl.

Examples of aryl groups and heterocyclic rings serving as such substituents are the same as those exemplified above.

When X is a sulfur atom, the sulfur atom may be in the form of a sulfoxide, sulfone or the like depending on the stage of oxidation.

The compound (I) may be such that the carboxyl group thereof may be in the form of a pharmacologically acceptable salt. Examples of such salts are those of alkali metals (sodium and potassium) and alkaline earth metals (calcium).

The leaving group represented by $Z^1$ in the formula (II) is, for example, hydroxyl. The leaving group $Z^2$ included in the formula (III) may be, for example, a hydrogen atom when $X'$ is an oxygen atom or sulfur atom [compound (III')], or $-SR^1$, when $X'$ is a sulfur atom [compound (III'')].

The compound (I) of the present invention can be prepared, for example, by the process shown below. Either one of different compounds (III) are usable as illustrated.

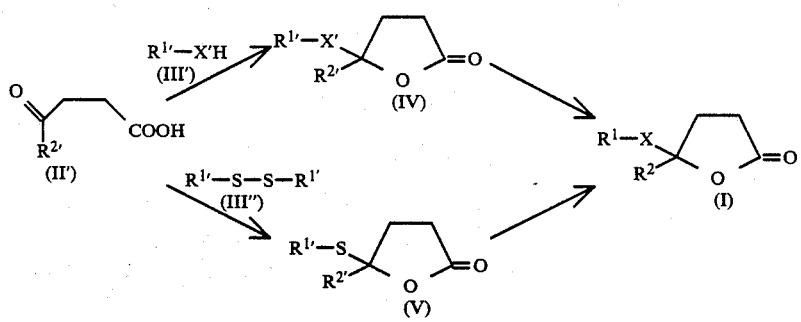

wherein $R^1$, $R^{1'}$, $R^2$, $R^{2'}$, X and X' are as defined above.

The process for preparing the compound (I) of the invention will be described below in detail.

The compound (II') can be reacted with the compound (III') usually in a solvent in the presence of a condensing agent to obtain the compound (IV). Examples of useful condensing agents are N,N'-dicyclohexylcarbodiimide (DCC), DCC-1-hydroxybenzotriazole (HOBT), 1-ethoxycarbonyl-2-ethoxy-1,2-dihydroxyquinoline (EEDQ), carbonyldiimidazole, diphenylphosphorylazide, etc. For this reaction, the compound (II') and the condensing agent are each used usually in an amount of about 1 mole per mole of the compound (II'), while an excess of the compound (III') as well as of the agent is usable insofar as the reaction can be conducted free of trouble. The present reaction is conducted usually in a solvent. Examples of useful solvents are common organic solvents such as dichloromethane, chloroform, 1,2-dichloroethane, dioxane, tetrahydrofuran, ethyl acetate, benzene, hexane, N,N-dimethylformamide and acetonitrile. These solvents are used singly or in admixture. The reaction temperature is usually about $-50°$ C. to about 150° C., preferably about $-30°$ C. to about 80° C. although not limited specifically insofar as the reaction proceeds. The reaction is conducted usually for several minutes to several tens of hours but may require several days in some cases.

The compound (II') can be reacted with the compound (III") usually in a solvent, such as one exemplified above, in the presence of a phosphine such as triphenylphosphine or tributylphosphine, to prepare the compound (V). For this reaction, the compound (III") and the phosphine are each used usually in an amount of about 1 mole per mole of the compound (II'). However, the former compounds are usable in an excess amount provided that the reaction can be carried out free of trouble. The reaction temperature is usually about $-50°$ C. to about 150° C., preferably about $-30°$ C. to about 80° C. The reaction time is generally several tens of minutes to several tens of hours.

When required, the compound (IV) (in the case where X'=S) and the compound (V) are subjected to an oxidizing reaction to give the compound (I) (X=SO or $SO_2$). The oxidizing agent to be used for this reaction is preferably a mild one, such as perbenzoic acid, ozone, hydrogen peroxide, selenium dioxide and sodium metaperiodate. It is more preferable to use a substituted perbenzoic acid such as metachloroperbenzoic acid. The reaction is conducted in a solvent, such as water, alcohol or dichloromethane, at $-50°$ C. to 50° C. for several minutes to several hours. An equivalent weight of the oxidizing agent is used based on the compound (IV) or (V), while an excess of the agent is usable insofar as no adverse effect results.

The pyridyl group in the substituent $R^1$ or $R^2$ of the compound (IV) or (V) can be quaternized in dimethylacetamide, acetonitrile or like polar solvent or such a solvent containing water, using a quaternizing agent such as an alkyl activated with a halogen (iodine, bromine or the like) or with an ester (3-oxobutyryloxy ester, phosphoric acid derivatives or the like). This reaction is conducted generally at room temperature. When desired, the reaction may be carried out in the presence of an inorganic salt such as potassium iodide. An intramolecular pyridinium salt can be formed by removing the protective group from the corresponding carboxyl group in the resulting pyridinium salt.

When the compound (IV) and the compound (V) have a protected carboxyl group, these compounds are subjected to a deprotecting reaction as required, whereby the compound (I) can be prepared. The protective group can be removed by a suitably selected conventional method as by using an acid or resorting to reduction under conditions that will not produce any adverse effect. Although the acid to be used for the method using an acid differs depending on the conditions employed, examples of useful acids are inorganic acids such as hydrochloric acid and sulfuric acid, and organic acids such as formic acid, acetic acid, trifluoroacetic acid and propionic acid. Also useful are acid ion exchange resins. It is especially suitable to use trifluoroacetic acid in the presence of anisole. An organic solvent such as dichloromethane may also be present in the reaction system.

Useful methods wherein reduction is resorted to include, for example, a method employing a metal such as zinc or tin, or a metal compound such as chromium dichloride or chromium acetate, and an organic or inorganic acid such as acetic acid, propionic acid or hydrochloric acid, and a reduction method which is practiced in the presence of a catalytic reducing metal catalyst. Examples of useful catalysts for the catalytic reduction method are a platinum wire, platinum sponge, platinum black, platinum oxide, colloidal platinum and like platinum catalysts, palladium sponge, palladium black, palladium oxide, palladium barium sulfate, palladium barium carbonate, palladium carbon, palladium silica gel, colloidal palladium and like palladium catalysts, reduced nickel, nickel oxide, Raney nickel, Urushibara nickel and the like. Further in another reduction method wherein a metal and an acid are used, the metal is iron, chromium or the like, and the acid is an inorganic acid such as hydrochloric acid or an organic acid such as formic acid, acetic acid or propionic acid. The reduction methods are practiced usually in a solvent. For example, frequently used for the catalytic reduction method are alcohols such as methanol, ethanol, propyl alcohol and isopropyl alcohol, ethyl acetate, tetrahydrofuranphosphoric acid buffer, etc. Although water, acetone and the like are generally used for the method employing a metal and an acid, the acid itself is also usable as a solvent when it is a liquid.

In the method using an acid and the reduction methods, the reaction is conducted usually with cooling or at room temperature.

When $R^2$ in the compound (I) is carboxyl, the compound is reacted with a primary amine or secondary amine, for example, with a compound represented by the formula

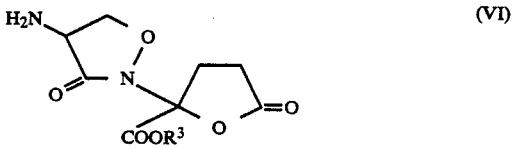

wherein $R^3$ is a protective group for the above-mentioned carboxyl group when so desired, whereby an amidated carboxylic derivative (TAN-588 derivative) can be prepared.

The amidation reaction, i.e. the reaction of the compound (I) with the compound (VI), can be conducted usually in a solvent. The compound (I) can be reacted as a free acid or as a derivative which is reactive at the carboxyl group. When in the form of a free acid, the compound (I) can be reacted with the compound (VI) in the presence of a condensing agent. Examples of useful condensing agent are N,N'-dicyclohexylcarbodiimide or like carbodiimide, carbonyldiimidazole, 1-ethoxycarbonyl-2-ethoxy-1,2-dihydroxyquinoline, diphenylphosphorylazide and the like.

Examples of useful derivatives which are reactive at the carboxyl group are acid halides, acid anhydrides, amide compounds, active esters, active thio esters, etc. More specific examples of such reactive derivatives are as follows.

(1) Acid halides

Examples of acid halides are acid chloride, acid bromide, etc.

(2) Acid anhydrides

Examples of acid anhydrides are mixed acid anhydride with a monoalkylcarbonic acid, mixed acid anhydride with an aliphatic carboxylic acid (such as acetic acid, pivalic acid, valeric acid, isovaleric acid or trichloroacetic acid), mixed acid anhydride with an aromatic carboxylic acid (such as benzoic acid), acid anhydride symmetric with the compound (I), etc.

(3) Amide compounds

Amide compounds composed of pyrazole, imidazole, 4-substituted imidazole, dimethylpyrazole, benzotriazole or the like, with the carboxyl group attached to the nitrogen on the ring thereof are used.

(4) Active esters

Examples of active esters are a methyl ester, ethyl ester, methoxymethyl ester, propargyl ester, 4-nitrophenyl ester, 2,4-dinitrophenyl ester, trichlorophenyl ester, pentachlorophenyl ester, mesylphenyl ester and the like. Also useful are esters with 1-hydroxy-1H-2-pyridone, N-hydroxysuccinimide, 1-hydroxybenzotriazole, N-hydroxy-5-norbornene-2,3-dicarboxylic acid imide, N-hydroxyphthalimide and the like.

(5) Active thio esters

Examples of useful active thio esters are those with 2-pyridylthiol, 2-benzthiazolylthiol and like heterocyclic thiols.

The desired reactive derivative is suitably selected from among these examples depending on the kind of carboxylic acid.

The present reaction is conducted sometimes in the presence of a base. Examples of useful bases are aliphatic tertiary amines such as trimethylamine, triethylamine, tripropylamine and tri-n-butylamine; tertiary amines such as N-methylpiperidine, N-methylpyrrolidone, cyclohexyldimethylamine and N-methylmorpholine; dialkylamines such as di-n-butylamine, diisobutylamine and dicyclohexylamine; aromatic amines such as pyridine, lutidine and γ-collidine; hydroxides or carbonates of alkali metals such as lithium, sodium and potassium and alkaline earth metals such as calcium and magnesium; etc.

For the present reaction, usually about 1 mole of the reactive carboxylic acid derivative of compound (I) is used per mole of the compound (VI). However, an excess of the derivative is also usable insofar as it is not detrimental to the reaction. When to be used, the base is used usually in an amount of about 1 mole to about 30 moles, preferably about 1 mole to about 10 moles, per mole of the compound (VI) although the amount is variable according to the kind of reactive carboxylic acid derivative and other reaction conditions. The present reaction is conducted usually in a solvent. Examples of useful solvents are ethers such as dioxane, tetrahydrofuran, diethyl ether, diiospropyl ether, propylene oxide and butylene oxide; esters such as ethyl acetate and ethyl formate; halogenated hydrocarbon halides such as chloroform, dichloromethane, 1,2-dichloroethane and 1,1,1-trichloroethane; hydrocarbons such as benzene, toluene and n-hexane; amides such as N,N-dimethylformamide and N,N-dimethylacetamide; nitriles such as acetonitrile; and like usual organic solvents. These solvents are used singly or in admixture. Among the bases exemplified above, those which are liquid are usable also as solvents. The reaction temperature, which is not limited specifically insofar as the reaction proceeds, is usually about −50° C. to about 150° C., preferably about −30° C. to about 80° C. The reaction is completed usually within several tens of minutes to several tens of hours but may require several tens of days in some cases, although the reaction time varies with the starting materials, base, reaction temperature and solvent used. When the carboxylic acid derivative thus amidated in a TAN-588 derivative, the product is subjected to a deprotecting reaction when desired, whereby the TAN-588 derivative can be obtained in the form of a carboxylic compound or salt thereof. The protective group can be removed by the same method as already described. The resulting compound is included also within the scope of compounds (I).

The compound (II'), starting material of the process of the invention, can be prepared from 2-oxoglutaric acid by selectively esterifying only one of its two carboxylic groups, i.e. the carboxylic group at the 1-position. This reaction is carried out by reacting 2-oxoglutaric acid with an approximately equivalent weight of esterifying agent in a solvent in the presence of an equivalent weight of base. Examples of useful esterifying agents are halides such as methyl iodide, benzyl bromide, p-nitrobenzyl bromide, m-phenoxybenzyl bromide, p-tert-butylbenzyl bromide, diphenylmethyl bromide and pivaloyloxymethyl chloride; dialkyl sulfates such as dimethyl sulfate and diethyl sulfate; etc. Examples of useful bases are diisopropylamine, dicyclohexylamine, cyclohexylisopropylamine, triethylamine, tripropylamine, tri-n-butylamine, diisopropylethylamine, DABCO, DBU, N-methylmorpholine, N-methylpiperidine, N-methylpyrrolidine, 3,4-dihydro-2H-pyrido[1,2-a]pyridine-2-one, 4-dimethylaminopyridine, pyridine, lutidine, γ-collidine and like organic amines; hydrides, hydroxides or carbonates of lithium, sodium, potassium, cesium and like alkali metals; etc.

Examples of useful solvents are N,N-dimethylformamide, N,N-dimethylacetamide, hexamethylphosphoramide, dimethyl sulfoxide, dichloromethane, acetonitrile, tetrahydrofuran and the like. The reaction temperature is usually about −20° C. to about 100° C. The reaction time is about 5 minutes to about 30 hours.

The starting compound of the formula (VI) is a known compound. Unexamined EPC Publication No. 0191989 disclosed a process for preparing this compound.

The compound (I), which provides the abovementioned TAN-588 derivative, can be useful intermediate for preparing the basic skeleton [2-(4-substituted amino-3-oxo-2-isoxazolidinyl)-5-oxo-2-tetrahydrofurancarboxylic acid derivative ] of TAN-588. More specifically, the reaction of the compound of the formula (I) wherein $R^2$ is a protected carboxylic group with a compound represented by the formula

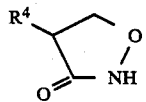

(VII)

wherein $R^4$ is a protected amino group, in a solvent in the presence of a base affords a compound of the formula

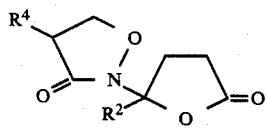

(VIII)

Examples of solvents useful for this reaction are those exemplified for the reaction between the compound (II') and the compound (III'). Examples of suitable bases for use in the reaction are organic amines such as trimethylamine, diisopropylethylamine, N-methylmorpholine, dicyclohexylamine, triethylenediamine, pyridine, 4-dimethylaminopyridine and imidazole; inorganic bases such as hydroxides of lithium, sodium, potassium and like alkali metals; etc. For the present reaction, about 1 mole of the compound (VII) and about 1 mole of the base are usually used per mole of the compound (I), while the compound (VII) and the bases are usable in excess amounts insofar as the reaction can be conducted free of any trouble. The base may be used in an amount suitable for use as a catalyst. The reaction temperature is generally −20° C. to 150° C., preferably 0° C. to 100° C., although not specifically limited insofar as the reaction proceeds. The reaction time is usually several tens of minutes to several tens of hours. When required, the compound (VIII) thus obtained can be subjected to a deprotecting reaction, amidation reaction, etc. in the same manner as already described and thereby converted to a TAN-588 derivative having antibacterial activity.

The desired compounds (I) thus obtained can be isolated and purified by known methods such as concentration, phase transfer, solvent extraction, freeze-drying, crystallization, recrystallization, fractionation, chromatography and the like.

When the desired compound (I) contains an asymmetric carbon, stereoisomers are present. These isomers and a mixture thereof are also included within the scope of the invention.

The compound (I) of the present invention can be reacted with a base to form a salt as already stated.

The present compound (I), when obtained in a free form, may be made into a salt by a usual method. When obtained in the form of a salt, the compound may be made into a free form by a usual method.

The compound (I) can be in the form of an intramolecular salt, which is also included within the invention.

Thus, the compounds (I) of the invention, salts, esters or amides thereof include those exhibiting antibacterial activity on some kinds of gram-positive bacteria and gram-negative bacteria and are low in toxicity. Accordingly, such compounds are usable as bacterial infection curing agents or antibacterial agents for mammals (such as mice, rats, dogs, cows, swine and man) for treating bacterial infections (such as infections of the respiratory system, urethral duct, bile duct and intestines, gynecological and surgical infections and suppurative diseases).

Furthermore, the compound (I) of the invention acts to inhibit 5-lipoxygenase metabolites (such as leukotrienes, 5-hydroxyeicosatetraenoic acid, 5-peroxyeicosatetraenoic acid and likoxines) and can be used as an agent for treating functional disorders of the heart, brain, lung, kidney, etc., circulation improving agent therefore, antiasthmatic agent and antiallergic agent.

The compound (I) or a salt thereof is given at a daily dosage of about 2 to about 100 mg/kg, preferably about 5 to about 40 mg/kg, calculated as the compound (I).

For oral administration, the compound (I) or a pharmacologically acceptable salt thereof can be mixed with a suitable pharmacologically acceptable carrier, excipient or diluent and then made into tablets, granules, drops, encapsulated preparation or the like by a conventional method. Alternatively, the compound or salt can be formulated into an injection solution by a usual method and then admixed with a sterilized carrier prepared by a usual method for parenteral administration.

Suitable for use in producing an oral preparation, e.g. tablets, are binders (such as hydroxypropylcellulose, hydroxypropylmethylcellulose and macrogol), disintegrators (such as starch and carboxymethylcellulose calcium), excipients (such as lactose and starch), lubricants (such as magnesium stearate and talc), etc.

Suitable for use in producing a parenteral preparation, e.g. an injection solution, are isotonic agents (such as glucose, D-sorbitol, D-mannitol and sodium chloride), antiseptics (such as benzyl alcohol, chlorobutanol, methyl p-oxybenzoate and propyl p-oxybenzoate), buffers (such as phosphate buffer and sodium acetate buffer), etc.

The present invention will be described in greater detail with reference to the following reference examples and examples, which, however, in no way limit the invention.

The symbols used for NMR are as follows. s stands for singlet, d for doublet, dd for double of doublets, t for triplet, ABq for AB quartet, m for multiplet and bs for broad singlet.

REFERENCE EXAMPLE 1

Preparation of 1-(4-nitrobenzyl) 2-oxoglutarate

To a solution of 2.93 g of 2-oxoglutaric acid in 20 ml of dimethylformamide was added 3.63 g of dicyclohexylamine, which was heated at 50° C. 4-Nitrobenzyl bromide (4.75 g) was added to the mixture and stirred for 15 min. at 70° C. After cooling, 100 ml of ethyl acetate was added to the mixture. The precipitated crystals were filtered off and washed with ethyl acetate. The combined solution of the filtrate and washings was washed with water and then saturated sodium chloride, and dried over MgSO$_4$. The solvent was removed under reduced pressure and the residue was subjected to silica gel column chromatography eluting with hexane-ethyl acetate-acetic acid (50:50:1) to yield 5.2 g of the title compound as crystals.
MP: 100°–102° C.
IR $\nu$max (KBr)cm$^{-1}$: 1735, 1707, 1530, 1345, 1275, 1085.
NMR (90 MHz, CDCl$_3$-DMSO-d$_6$) $\delta$: 2.5–2.8 (2H, m), 2.9–3.3 (2H, m), 5.40 (2H, s), 7.62 (2H, d, J=9 Hz), 8.28 (2H, d, J=9 Hz).

REFERENCE EXAMPLE 2

Preparation of 1-diphenylmethyl 2-oxoglutrate

The title compound (3.2 g) as crystals was obtained from 2.93 g of 2-oxoglutaric acid, 4.75 g of diphenylmethyl bromide and 3.63 g of dicyclohexylamine in a similar way to Reference Example 1.
MP: 107°–109° C.
IR $\nu$max (KBr)cm$^{-1}$: 1730, 1710.
NMR (60 MHz, CDCl$_3$) $\delta$: 2.58–3.17 (4H, m), 6.99 (1H, s), 7.31–7.54 (10H, m).

REFERENCE EXAMPLE 3

Preparation of 1-benzyl 2-oxoglutarate

The title compound was obtained in a similar way to Reference Example 1.
MP: 51°–52° C.
IR $\nu$max (Nujol)cm$^{-1}$: 1740, 1705, 1270, 1090, 1040.
NMR (90 MHz, CDCl$_3$) $\delta$: 2.67 (2H, t, J=6 Hz), 2.97 (2H, m), 5.26 (2H, s), 7.35 (5H, s), 8.9 (1H, b).

REFERENCE EXAMPLE 4

Preparation of 1-methyl 2-oxoglutarate

The title compound was obtained in a similar way to Reference Example 1.
MP: 54.5°–55.0° C.
IR $\nu$max (KBr)cm$^{-1}$: 3430, 1750, 1735, 1710, 1275, 1255 1225, 1080.
NMR (90 MHZ, CCDl$_3$) $\delta$: 2.60–3.27 (4H, m), 3.88 (3H, s), 8.20 (1H, bs).

REFERENCE EXAMPLE 5

Preparation of 1-pivaloyloxymethyl 2-oxoglutarate

The title compound was obtained in a similar way to Reference Example 1.
IR $\nu$max (Neat)cm$^{-1}$: 2970, 1750, 1710.
NMR (90 MHZ, CDCl$_3$)$\delta$: 1.24 (9H, s), 2.67–3.19 (4H, m), 5.89 (2H, s).

REFERENCE EXAMPLE 6

Preparation of 1-(2-trimethylsilylethyl) 2-oxoglutarate

The title compound was obtained in a similar way to Reference Example 1.
IR$\nu$max (Neat)cm$^{-1}$: 1730, 1420, 1250, 1080, 1030, 840.
NMR (100 MHZ, CDCl$_3$)$\delta$: 0.80–1.20 (2H, m), 2.50–2.85 (2H, m), 2.98–3.20 (2H, m), 4.16–4.44 (2H, m).

REFERENCE EXAMPLE 7

Preparation of 5-pyrrolidinyl-4,5-dioxopentanoic acid

To a solution of 584 mg of 2-oxoglutaric acid in 10 ml of acetonitrile was added 824 mg of N,N'-dicyclohexylcarbodiimide (DCC), which was stirred for 10 min. at room temperature. Then 284 mg of pyrrolidine was added to the mixture and stirred for 10 minutes at room temperature. The precipitated crystals were filtered off and the fitrate after addition of ethyl acetate was extracted with an aqueous sodium hydrogen carbonate solution. The extract was adjusted to pH 3.0 by addition of 2N-hydrochloric acid and extracted with ethyl acetate. The organic phase was washed with water, dried (MgSO$_4$) and concentrated. The residue was subjected to silica gel chromatography to obtain 412 mg of the title compound as colorless crystals.
MP: 101°–102° C.
IR $\nu$max (KBr)cm$^{-1}$: 2970, 1730, 1710, 1600, 1390, 1330, 1210, 1170.
NMR (90 MHz, CDCl$_3$) $\delta$: 1.81–2.06 (4H, m), 2.65–2.84 (2H, m), 3.08–3.27 (2H, m), 3.43–3.80 (4H, m), 8.60–9.01 (1H, m).

EXAMPLE 1

Preparation of 4-nitrobenzyl 2-phenoxy-5-oxo-2-tetrahydrofurancarboxylate
[Compound (1)]

Phenol (941 mg), 1-(4-nitrobenzyl) 2-oxoglutarate (3.09 g) and DCC (2.27 g) were dissolved in 100 ml of dichloromethane and stirred for 3 hours at room temperature. The precipitated crystals were filtered off and the filtrate was subjected to silica gel column chromatography eluting with dichloromethane-ethyl acetate (3:1) to obtain 1.55 g of the title compound.
MP: 145°–146° C.
IR $\nu$max (KBr)cm$^{-1}$: 1790, 1750, 1510, 1480, 1350, 1260, 1190, 1040.
NMR (90 MHz, CDCl$_3$)$\delta$: 2.45–2.95 (4H, m), 5.22 (2H, ABq, J=12, 18 Hz), 6.95–7.35 (7H, m), 8.00–8.20 (2H, d, J=9 Hz).

EXAMPLE 2

Preparation of benzyl 2-phenoxy-5-oxo-2-tetrahydrofurancarboxylate
[Compound (B 2)]

The title compound (2), (1.13 g) was obtained from 941 mg of phenol, 2.36 g of 1-benzyl 2-oxoglutarate and 2.06 g of DCC by a similar method to Example 1.
MP: 57°–79° C.
IR $\nu$max (KBr)cm$^{-1}$: 1790, 1760, 1580, 1490, 1290, 1270, 1210, 1190, 1170, 1060.
NMR (90 MHz, CDCl$_3$) $\delta$: 2.40–2.95 (4H, m), 5.15 (2H, s), 6.90–7.40 (10H, m).

EXAMPLE 3

Preparation of 2-phenoxy-5-oxo-2-tetrahydrofurancarboxylic acid [Compound (3)]

To a mixture of 500 mg of Compound (1) obtained by Example 1, 2 ml of tetrahydrofuran, 10 ml of ethyl acetate and 12 ml of phosphate buffer (pH 7) was added 300 mg of 10% palladium-carbon. The mixture was stirred for an hour at room temperature in a stream of hydrogen. After filtering the catalyst off, ethyl acetate was added to the filtrate and the aqueous phase was collected. The aqueous phase was adjusted to pH 3 by addition of 2N-HCl and extracted with ethyl acetate. The extract was washed with saturated sodium chloride solution and distilled off the solvent under reduced pressure to obtain 227 mg of the title compound (3).

MP: 113°–114° C.

IR$\nu$max (KBr)cm$^{-1}$: 3000, 1800, 1750, 1490, 1190, 1040.

NMR (90 MHz, CDCl$_3$)$\delta$: 2.62 (4H, s), 6.92–7.37 (5H, m), 9.41 (1H, bs).

EXAMPLE 4

Preparation of benzyl 2-methoxy-5-oxo-2-tetrahydrofurancarboxylate [Compound (4)]

The title compound (4), (1.5 g) was obtained from 700 mg of methanol, 2.36 g of 1-benzyl 2-oxoglutarate and 2.1 g of DCC by a similar method to Example 1.

MP: 39°–41° C.

IR$\nu$max (KBr)cm$^{-1}$: 1800, 1760, 1450, 1380, 1270, 1200, 1170, 1030.

NMR (90 MHz, CDCl$_3$)$\delta$: 2.30–2.90 (4H, m), 3.46 (3H, s), 5.33 (2H, s), 7.46 (5H, s).

EXAMPLE 5

Preparation of benzyl 2-phenylthio-5-oxo-2-tetrahydrofurancarboxylate [Compound (5)]

The title compound (5), (1.85 g) was obtained from 1.03 g of thiophenol, 2.21 g of 1-benzyl 2-oxoglutarate and 1.94 g of DCC by a similar method to Example 1.

MP: 105°–107° C.

IR$\nu$max (KBr)cm$^{-1}$: 1790, 1740, 1450, 1360, 1250, 1160, 1050.

NMR (90 MHz, CDCl$_3$)$\delta$: 2.30–2.80 (4H, m), 5.03 (2H, s), 7.10–7.55 (10H, m).

EXAMPLE 6

Preparation of benzhydryl 2-phenylthio-5-oxo-2-tetrahydrofurancarboxylate [Compound (6)]

A mixture of 850 mg of thiophenol, 2.21 g of 1-benzyl 2-oxoglutarate, 1.58 g of 1-ethoxycarbonyl-2-ethoxy-1,2-dihydroquinoline (EEDQ) and 60 ml of dichloroethane was stirred for 20 hours at room temperature. The reaction mixture was subjected to silica gel column chromatography eluting with hexane-dichloromethane (1:3) to give 1.13 g of the title compound (6).

MP: 157°–159° C.

IR$\nu$max (KBr)cm$^{-1}$: 1790, 1740, 1440, 1240, 1160, 1050.

NMR (90 MHz, CDCl$_3$)$\delta$: 2.35–3.00 (4H, m), 6.77 (1H, s), 7.00–7.48 (15H, m).

EXAMPLE 7

Preparation of 4-nitrobenzyl 2-phenylthio-5-oxo-2-tetrahydrofurancarboxylate [Compound (7)]

The title compound (7), (770 mg) was obtained from 550 mg of thiophenol, 1.15 g of 1-(4-nitrobenzyl) 2-oxoglutarate and 1.15 g of DCC by a similar method to Example 1.

MP: 101°–102° C.

IR$\nu$max (KBr)cm$^{-1}$: 1800, 1750, 1520, 1340, 1240, 1160, 1060.

NMR (90 MHz, CDCl$_3$)$\delta$: 2.38–3.00 (4H, m), 5.06 (2H, s), 7.05–7.55 (7H, m), 8.10 (2H, d, J=9 Hz).

EXAMPLE 8

Preparation of 2-trimethylsilylethyl 2-phenylthio-5-oxo-2-tetrahydrofurancarboxylate [Compound (8)]

The title compound (8), (425 mg) was obtained from 231 mg of thiophenol, 430 mg of 1-(2-trimethylsilylethyl) 2-oxoglutarate and 432 mg of DCC by a similar method to Example 1.

MP: 56°–57° C.

IR$\nu$max (KBr)cm$^{-1}$: 1780, 1720, 1290, 1240, 1160, 1060.

NMR (90 MHz, CDCl$_3$)$\delta$: 0.80 (2H, m), 2.35–2.90 (4H, m), 4.10 (2H, dd, J=7, 10 Hz), 7.20–7.65 (5H, m).

EXAMPLE 9

Preparation of 4-nitrobenzyl 2-(4-chlorophenyl)thio-5-oxo-2-tetrahydrofurancarboxylate [Compound (9)]

The title compound (9), (3.0 g) was obtained from 1.45 g of 4-chlorothiophenol, 3.1 g of 1-(4-nitrobenzyl) 2-oxoglutarate and 2.3 g of DCC by a similar method to Example 1.

MP: 176°–178° C.

IR$\nu$max (KBr)cm$^{-1}$: 1790, 1730, 1510, 1470, 1140, 1290, 1160, 1060.

NMR (90 MHz, CDCl$_3$)$\delta$: 2.40–2.95 (4H, m), 5.14 (2H, s), 7.15–7.50 (6H, m), 8.21 (2H, d, J=9 Hz).

EXAMPLE 10

Preparation of benzhydryl 2-(4-chlorophenyl)thio-5-oxo-2-tetrahydrofurancarboxylate [Compound (10)]

The title compound (10), (1.27 g) was obtained from 725 mg of 4-chlorothiophenol, 1.71 g of 1-benzhydryl 2-oxoglutarate and 1.15 g of DCC by a similar method to Example 1.

MP: 153°–155° C.

IR$\nu$max (KBr)cm$^{-1}$: 1800, 1750, 1250, 1170, 1060.

NMR (90 MHz, CDCl$_3$)$\delta$: 2.40–2.83 (4H, m), 6.81 (1H, s), 7.03–7.41 (14H, m).

EXAMPLE 11

Preparation of 2-(4-chlorophenol)thio-5-oxo-2-tetrahydrofurancarboxylic acid [Compound (11)]

To a solution of 439 mg of Compound (10) in 10 ml of dichloromethane were added 0.9 ml of anisole and 1 ml of trifluoroacetic acid, followed by stirring for 2 hours. The reaction mixture was concentrated under reduced pressure to obtain 220 mg of the title compound (11).

MP: 143°–145° C.

IRνmax (KBr)cm$^{-1}$: 3100, 1770, 1740, 1470, 1190, 1030.

NMR (90 MHz, CDCl$_3$)δ: 2.34–3.96 (4H, m), 7.39 (4H, ABq, J=9, 18 Hz).

EXAMPLE 12

Preparation of 4-nitrobenzyl 2-(2-pyridyl)methylthio-5-oxo-2-tetrahydrofurancarboxylate [Compound (12)]

The title compound (12) (2.8 g) was obtained from 1.25 g of 2-pyridylmethanethiol, 3.1 g of 1-(4-nitrobenzyl) 2-oxoglutarate and 2.3 g of DCC by a similar method to Example 1.

IRνmax (KBr)cm$^{-1}$: 1780, 1740, 1520, 1430, 1340, 1250, 1160, 1060.

NMR (90 MHz, CDCl$_3$)δ: 2.35–2.95 (4H, s), 4.12 (2H, s), 5.28 (2H, s), 7.10–8.70 (8H, m).

EXAMPLE 13

Preparation of 2-(2-pyridyl)methylthio-5-oxo-2-tetrahydrofurancarboxylic acid [Compound (13)]

To a mixture of 777 mg of Compound (12), 20 ml of ethyl acetate and 20 ml of phosphate buffer (pH 7) was added 1 g of 10% palladium-carbon and the mixture was stirred at room temperature for 4 hours in a stream of hydrogen. After filtering the catalyst off, ethyl acetate was added to the mixture. The collected aqueous phase was adjusted to pH 3 by addition of 2N-HCl and concentrated under reduced pressure. Methanol was added to the residue, and after filtering an insoluble material off, the filtrate was concentrated under reduced pressure. Ethyl ether was added to the residue to obtain 356 mg of the title compound (13).

IRνmax (KBr)cm$^{-1}$: 3400, 1760–1780, 1605, 1460, 1180, 1050.

EXAMPLE 14

Preparation of 4-nitrobenzyl 2-(4-pyridyl)thio-5-oxo-2-tetrahydrofurancarboxylate [Compound (14)]

The title compound (14), (740 mg) was obtained from 1.11 g of 4-pyridinethiol, 3.09 g of 1-(4-nitrobenzyl) 2-oxoglutarate and 2.27 g of DCC by a similar method to Example 1.

MP: 118°–119° C.

IRνmax (KBr)cm$^{-1}$: 1800, 1740, 1570, 1520, 1340, 1250, 1160, 1045.

NMR (90 MHz, CDCl$_3$)δ: 2.45–3.00 (4H, m), 5.16 (2H, s), 7.25–7.45 (4H, m), 8.16 (2H, d, J=9 Hz) 8.46 (2H, d, J=6 Hz).

EXAMPLE 15

Preparation of 2-(4-pyridyl)thio-5-oxo-2-tetrahydrofurancarboxylic acid [Compound (15)]

The title compound (15), (302 mg) was obtained from 650 mg of Compound (14) by a similar method to Example 13.

IRνmax (KBr)cm$^{-1}$: 3100, 1790, 1770, 1650, 1480, 1160, 1050.

EXAMPLE 16

Preparation of 4-nitrobenzyl 2-(4-pyridyl)methylthio-5-oxo-2-tetrahydrofurancarboxylate [Compound (16)]

The title compound (16) was obtained from 1.0 g of 4-pyridylmethanethiol, 2.5 g of 1-(4-nitrobenzyl)-2-oxoglutarate and 1.9 g of DCC by a similar method to Example 1.

IRνmax (KBr)cm$^{-1}$: 1800, 1740, 1600, 1520, 1350, 1250, 1160, 1060.

NMR (90 MHz, CDCl$_3$)δ: 2.35–2.95 (4H, m), 3.95 (2H, s), 5.12 (2H, s), 7.15–8.60 (8H, m).

EXAMPLE 17

Preparation of pivaloyloxymethyl 2-(2-acetamidoethyl)thio-5-oxo-2-tetrahydrofurancarboxylate [Compound (17)]

The title compound (17), (4.0 g) was obtained from 1.2 g of 2-acetamidoethanethiol, 3.1 g of 1-pivaloyloxymethyl 2-oxoglutarate and 2.3 g of DCC by a similar method to Example 1.

IRνmax (KBr)cm$^{-1}$: 3300, 1800, 1755, 1650, 1540, 1280, 1180, 1020.

NMR (90 MHz, CDCl$_3$)δ: 1.26 (9H, s), 1.94 (3H, s), 2.29–2.98 (6H, m), 3.43 (2H, m), 5.88 (2H, s), 6.61 (1H, bs).

EXAMPLE 18

Preparation of 4-nitrobenzyl 2-(2-pyridyl)thio-5-oxo-2-tetrahydrofurancarboxylate [Compound (18)]

A solution of 220 mg of 2,2'-dipyridyl disulfide, 281 mg of 1-(4-nitrobenzyl) 2-oxoglutarate and 263 mg of triphenylphosphine in 5 ml of dichloromethane was stirred for 20 hours at room temperature. The reaction mixture was subjected to silica gel column chromatography eluting with dichloromethane-ethyl acetate (9:1) to obtain 300 mg of the title compound (18).

MP: 75°–76° C.

IRνmax (KBr)cm$^{-1}$: 1790, 1750, 1510, 1350, 1270, 1180, 1160, 1120.

NMR (90 MHz), CDCl$_3$)δ: 2.50–3.20 (4H, m), 5.30 (2H, s), 6.95–8.30 (8H, m).

EXAMPLE 19

Preparation of benzyl 2-(2-pyridyl)thio-5-oxo-2-tetrahydrofurancarboxylate [Compound (19)]

The title compound (19), (2.8 g) was obtained from 2.2 g of 2,2'-dipyridyl disulfide, 2.36 g of 1-benzyl 2-oxoglutarate and 2.63 g of triphenylphosphine by a similar method to Example 18.

IRνmax (Neat)cm$^{-1}$: 1800, 1750, 1580, 1450, 1420, 1260, 1160, 1110, 1050.

NMR (90 MHz, CDCl$_3$)δ: 2.70–2.85 (4H, m), 5.04 (2H, s), 7.05–8.30 (9H, m).

EXAMPLE 20

Preparation of 4-nitrobenzyl 2-(2-benzothiazolyl)thio-5-oxo-2-tetrahydrofurancarboxylate [Compound (20)]

The title compound (20), (190 mg) was obtained from 369.4 mg of 2,2'-dibenzothiazolyl disulfide, 281 mg of 1-(4-nitrobenzyl) 2-oxoglutarate and 263 mg of triphenylphosphine by a similar method to Example 18.

IRνmax (KBr)cm⁻¹: 1780, 1740, 1520, 1350, 1260, 1170, 1050, 1000.

NMR (90 MHz, CDCl₃)δ: 2.50–3.10 (4H, m), 5.24 (2H, s) 7.15–8.30 (8H, m).

EXAMPLE 21

Preparation of benzyl 2-phenylthio-5-oxo-2-tetrahydrofurancarboxylate [Compound (5)]

The compound (5), (104 mg) was obtained from 220 mg of diphenyl disulfide, 236 mg of 1-benzyl 2-oxoglutarate and 263 mg of triphenylphosphine by a similar method to Example 18.

EXAMPLE 22

Preparation of benzhydryl 2-phenylsulfinyl-5-oxo-2-tetrahydrofurancarboxylate [Compound (22)]

A solution of 100 mg of Compound (6) and 43 mg of metachloroperbenzoic acid in 6 ml of dichloromethane was stirred for 0.5 hour under ice-cooling. The reaction mixture was poured into aqueous sodium hydrogen carbonate solution and extracted with ethyl acetate. The organic phase was washed with saturated sodium chloride solution and dried (MgSO₄). After distilling the solvent under reduced pressure, the residue was subjected to silica gel column chromatography eluting with hexane-ethyl acetate (2:1) to obtain 78 mg of the title compound (22).

IRνmax (Neat)cm⁻¹: 1800, 1760, 1740, 1490, 1440, 1100.

NMR (90 MHz, CDCl₃)δ: 2.33–3.42 (4H, m), 6.83 (1H, s), 7.03–7.76 (15H, m).

EXAMPLE 23

Preparation of 4-nitrobenzyl 2-phenylsulfinyl-5-oxo-2-tetrahydrofurancarboxylate [Compound (23)]

The title compound (23), (283 mg) was obtained from 374 mg of Compound (7) and 230 mg of metachloroperbenzoic acid by a similar method to Example 22.

IRνmax (Neat)cm⁻¹: 1800, 1760, 1734, 1490, 1450, 1100.

NMR (90 MHz, CDCl₃)δ: 2.35–3.45 (4H, m), 5.10 (2H, s), 7.05–7.65 (7H, m), 8.25 (2H, d, J=9 Hz).

EXAMPLE 24

Preparation of benzhydryl 2-phenylsulfonyl-5-oxo-2-tetrahydrofurancarboxylate [Compound (24)]

A solution of 658 mg of Compound (6) and 924 mg of metachloroperbenzoic acid in 10 ml of dichloromethane was allowed to stand overnight at −5° C. Then, the mixture was treated in a similar way to Example 22 to obtain 567 mg of the title compound (24).

IRνmax (Neat)cm⁻¹: 1820, 1730, 1570, 1330, 1250, 1150.

NMR (90 MHz, CDCl₃)δ: 2.53–3.30 (4H, m), 6.80 (1H, s), 7.10–7.70 (15H, m).

EXAMPLE 25

Preparation of sodium 2-[(4S)-4-(5-oxo-2-phenoxy-2-tetrahydrofuranylcarbonylamino)-3-oxo-2-isoxazolidinyl]-5-oxo-2-tetrahydrofurancarboxylate [Compound (25)]

(a) A mixture of 222 mg of Compound (3), 250 mg of benzhydryl 2-[(4S)-4-amino-3-oxo-2-isoxazolidinyl]-5-oxo-2-tetrahydrofurancarboxylate, 206 mg of DCC and 206 mg of 1-hydroxybenzotriazole (HOBT) in 4 ml of DMF was stirred for an hour at room temperature. The reaction mixture was poured into water and extracted with ethyl acetate. The organic phase was washed with water, dried (Na₂SO₄) and then distilled under reduced pressure to remove the solvent. The residue was subjected to silica gel column chromatography eluting with hexane-ethyl acetate (2:3) to yield 284 mg of benzhydrylester of the title compound (25).

IRνmax (KBr)cm⁻¹: 3340, 2930, 1800, 1740, 1695, 1520, 1180, 1050.

NMR (90 MHz, CDCl₃)δ: 2.31–3.30 (8H, m), 3.41–4.20 (1.5H, m), 4.46–4.93 (1.5H, m), 6.98 (1H, s), 7.11–7.58 (15H, m).

(b) The above product (284 mg) was dissolved in a mixture of 5 mg of tetrahydrofuran and 5 ml of phosphate buffer (pH 7). After adding 284 mg of 5% palladium-carbon, the mixture was stirred for 45 minutes at 0° C. in a stream of hydrogen. The mixture was filtered to remove the catalyst and the filtrate was concentrated. The concentrate was subjected to XAD-2 column chromatography, and the 10% ethanol eluate was concentrated and lyophilized to obtain 139 mg of the title compound (25).

IR νmax (KBr) cm⁻¹: 3400, 1800, 1790, 1720, 1650, 1380, 1190, 1040.

NMR (100 MHz, D₂O) δ: 2.41–3.29 (8H, m), 3.92–4.13 (1H, m), 4.42–4.78 (1H, m), 4.88–5.12 (1H, m), 7.11–7.57 (5H, m).

EXAMPLE 26

Preparation of sodium 2-{(4)-4-[(2-(4-chlorophenyl)thio-5-oxo-2-tetrahydrofuranylcarbonylamino]-3-oxo-2-isoxazolidinyl}-5-oxo-2-tetrahydrofurancarboxylate [Compound (26)]:

(a) Benzhydrylester of the title compound (26), (287 mg) was obtained from 200 mg of Compound (11) and 200 mg of benzhydryl 2-[(4S)-4-amino-3-oxo-2-isozazolidinyl]-5-oxo-2-tetrahydrofurancarboxylate by a similar method to Example 25 (a).

IR νmax (KBr) cm⁻¹: 3340, 2940, 1800, 1750, 1690, 1520, 1180, 1050.

NMR (90 MHz, CDCl₃) δ: 2.29–3.38 (8H, m), 3.41–4.89 (3H, m), 6.96 (1H, s), 7.15–7.52 (14H, m).

(b) To a solution of 287 mg of the above product in 20 ml of dichloromethane were added 0.49 ml of trifluoroacetic acid and 0.4 ml of anisole at −10°–−15° C., followed by stirring for 4 hours. The reaction mixture was concentrated and the residue was subjected to XAD-2 column chromatography. The 20% ethanol eluate was concentrated and lyophilized to obtain 137 mg of the title compound (26).

IR νmax (KB4)cm⁻¹: 3400, 1800, 1720, 1660, 1380, 1190, 1010.

NMR (100 MHz, D₂O) δ: 2.39–3.59 (8H, m), 3.79–4.09 (1H, m), 4.21–4.62 (1H, m), 4.81–5.12 (1H, m), 7.53–7.64 (4H, m)

EXAMPLE 27

Preparation of sodium 2-{(4S)-4-[5-oxo-2-(2-pyridyl)methylthio-2-tetrahydrofuranylcarbonylamino]-3-oxo-2-isoxazolidinyl}-5-oxo-2-tetrahydrofurancarboxylate [Compound (27)]

Benzhydrylester of the title compound (27), (210 mg) was obtained from 253 mg of Compound (13) and 200 mg of benzhydryl 2-[(4S)-4-amino-3-oxo-2-isoxazolidinyl]-5-oxo-2-tetrahydrofurancarboxylate by a similar method to Example 25 (a).

IR $\nu$max (KBr)cm$^{-1}$: 3340, 2930, 1800, 1750, 1690, 1520, 1180, 1050.

NMR (90 MHz, CDCl$_3$) δ: 2.21–3.42 (8H, m), 3.81–4.40 (3.5H, m), 4.45–5.13 L(1.5H, m), 6.93 (1H, s), 7.07–8.45 (14H, m).

The title compound (27), (53 mg) was obtained from 210 mg of the above product by a similar method to Example 26 (b).

IR $\nu$max (KBr)cm$^{-1}$: 3400, 1790, 1720, 1660, 1380, 1190, 1030.

NMR (100 MHz, D$_2$O) δ: 2.44–3.31 (8H, m), 4.0–4.27 (1H, m), 4.15 (2H, s), 4.48–4.78 (1H, m), 4.88–5.13 (1H, m), 7.40–8.55 (4H, m).

EXAMPLE 28

Preparation of sodium 2-{(4S)-4-[5-oxo-2-(4-pyridyl)thio-2-tetrahydrofuranylcarbonylamino]-3-oxo-2-isoxazolidinyl}-5-oxo-2-tetrahydrofurancarboxylate [Compound (28)]

Benzhydryl ester of the title compound (28), (184 mg) was obtained from 239 mg of Compound (15) and 200 mg of benzhydryl 2-[(4S)-4-amino-3-oxo-2-isoxazolidinyl]-5-oxo-2-tetrahydrofurancarboxylate by a similar method to Example 25 (a).

IR $\nu$max (KBr)cm$^{-1}$: 3340, 2930, 1800, 1750, 1690, 1520, 1180, 1050.

NMR (90 MHz, CDCl$_3$) δ: 2.35–3.30 (8H, m), 3.41–4.21 (1.5H, m), 4.45–4.92 (1.5H, m), 6.93 (1H, s), 7.21–8.52 (14H, m).

The title compound (28), (41 mg) was obtained from 184 mg of the above product by a similar method to Example 26 (b).

IR $\nu$max (KBr)cm$^{-1}$: 3400, 1800, 1720, 1650, 1380, 1190, 1050.

NMR (100 MHz, D$_2$O) δ: 2.41–3.29 (8H, m). 3.93–4.22 (1H, m), 4.41–7.78 (1H, m), 4.88–5.15 (1H, m), 7.88–8.68 (4H, m).

EXAMPLE 29

Preparation of benzhydryl 2-[(4S)-4-benzyloxycarbonylamino-3-oxo-2-isoxazolidinyl]-5-oxo-2-tetrahydrofurancarboxylate [Compound (29)]

A mixture of 46 mg of Compound (22), 26 mg of (4S)-4-benzyloxycarbonylamino-3-isoxazolidinone and 12 mg of triethylamine in 1 ml of dichloromethane was stirred for an hour at room temperature. The reaction mixture was poured into dilute hydrochloric acid and extracted with ethyl acetate. The organic phase was dried (MgSO$_4$) and concentrated under reduced pressure. The residue was subjected to thin-layer chromatography using hexane-ethyl acetate (1:1), to afford 17 mg of the title compound (29).

IR $\nu$max (KBr)cm$^{-1}$: 2950, 1780, 1700, 1530, 1300, 1260.

NMR (90 MHz, CDCl$_3$) δ: 2.30–3.36 (4H, m), 3.92–4.26 (1H, m), 4.53–4.76 (2H, m), 5.11 (2H, s), 6.97 (1H, s), 7.26–7.60 (15H, m).

EXAMPLE 30

Preparation of Compound (29)

A mixture of 48 mg of Compound (24), 27 mg of (4S)-4-benzyloxycarbonylamino-3-isoxazolidinone and 13 mg of triethylamine in 1 ml of dichloromethane was stirred for 4 hours at room temperature. The mixture was subjected to a similar workup to Example 29 to obtain 33 mg of Compound (29). This product was completely identical with IR and NMR spectra of the compound obtained by Example 29.

EXAMPLE 31

Preparation of 4-nitrobenzyl 2-[(4S)-4-benzyloxycarbonylamino-3-oxo-2-isoxazolidinyl]-5-oxo-2-tetrahydrofurancarboxylate [Compound (31)]

The title compound (31), (23.5 mg) was obtained from 55 mg of Compound (23), 33 mg of (4S)-4-benzyloxycarbonylamino-3-isoxazolidinone and 15 mg of triethylamine by a similar method to Example 30.

IR $\nu$max (Neat)cm$^{-1}$: 3350, 1800, 1770–1700, 1520, 1340, 1260, 1230, 1180, 1050.

NMR (90 MHz, CDCl$_3$) δ: 2.30–3.30 (4H, m), 4.1 (1H, m), 4.50–4.80 (2H, m), 5.11 (2H, s), 5.30 (1H, bs), 5.37 (2H, s), 7.35 (5H, s), 7.53 (2H, d, J=9 Hz), 8.23 (2H, d, J=9 Hz).

EXAMPLE 32

Preparation of benzyl 2-[(4S)-4-benzyloxycarbonylamino-3-oxo-2-isoxazolidinyl]-5-oxo-2-tetrahydrofurancarboxylate [Compound (32)]

(a) A mixture of 312 mg of Compound (2), 238 mg of (4S)-4-benzyloxycarbonylamino-3-isoxazolidinone and 5 mg of sodium hydroxide (fine powder) in 25 ml of tetrahydrofuran was refluxed for 2 hours. The reaction mixture was poured into dilute hydrochloric acid and extracted with ethyl acetate. The organic phase was dried (MgSO$_4$) and concentrated under reduced pressure. The residue was subjected to silica gel column chromatography using an eluent of hexane-ethyl acetate (2:1) to obtain 176 mg of the title compound (32).

IR $\nu$max (Neat)cm$^{-1}$: 1800, 1760–1700, 1520, 1180, 1050

NMR (90 MHz, CDCl$_3$) δ: 2.35–2.80 (4H, m), 4.00–4.20, (1H, m), 4.60–4.80 (2H, m), 5.10 (2H, s), 5.26 (2H, s), 7.33 (10H, s).

(b) A mixture of 317 mg of Compound (2), 353 mg of (4S)-4-benzyloxycarbonylamino-3-isoxazolidinone and 0.23 ml of triethylamine in 15 ml of tetrahydrofuran was refluxed for 8 hours, followed by a similar workup to Example 38 (a) to obtain 170 mg of Compound (32).

EXAMPLE 33

Preparation of Compound (32)

(a) A mixture of 120 mg of Compound (5), 70 mg of (4S)-4-benzyloxycarbonylamino-3-isoxazolidinone and 2 mg of sodium hydroxide (fine powder) in 6 ml of tetrahydrofuran was refluxed for 6 hours, followed by a similar workup to Example 32 (a) to obtain 30 mg of Compound (32).

(b) A mixture of 177 mg of Compound (5), 127 mg of (4S)-4-benzyloxycarbonylamino-3-isoxazolidinone and 0.1 ml of triethylamine in 20 ml of tetrahydrofuran was refluxed for 3 hours, followed by a similar workup to Example 32 (a) to obtain 29 mg of Compound (32).

2-Oxoglutaric acid half-esters [Compound (II)] were reacted with thiols [Compound (III)] in the presence of DCC in a similar way to Example 5 to obtain Compound (34–47) of the following examples.

EXAMPLE 34

Preparation of benzyl 2-benzylthio-5-oxo-2-tetrahydrofurancarboxylate [Compound (34)]

MP: 74°–75° C.

IR $\nu$max (KBr)cm$^{-1}$: 1785, 1730, 1165, 1065.

NMR (90 MHz, CDCl$_3$) $\delta$: 2.20–290 (4H, m), 3.90 (2H, ABq, J=13.5, 4.5 Hz), 5.13 (2H, s), 5.27–7.40 (10H, m).

EXAMPLE 35

Preparation of benzyl 2-(4-chlorophenyl)thio-5-oxo-2-tetrahydrofurancarboxylate [Compound (35)]

MP: 75°–76° C.

IR $\nu$max (KBr)cm$^{-1}$: 1790, 1750, 1735, 1165, 1180, 1060.

NMR (90 MHz, CDCl$_3$) $\delta$: 2.35–2.85 (4H, m), 5.05 (2H, s). 7.10–7.45 (9H, m).

EXAMPLE 36

Preparation of benzyl 2-(2-chlorophenyl)thio-5-oxo-2-tetrahydrofurancarboxylate [Compound (36)]

MP: 54°–55° C.

IR $\nu$max (KBr)cm$^{-1}$: 1790, 1750, 1250, 1170, 1050.

NMR (90 MHz, CDCl$_3$) $\delta$: 2.39–2.88 (4H, m), 5.09 (2H, s), 7.08–7.66 (9H, m).

EXAMPLE 37

Preparation of methyl 2-phenylthio-5-oxo-2-tetrahydrofurancarboxylate [Compound (37)]

MP: 70° C.

IR $\nu$max (KBr)cm$^{-1}$: 1800, 1780, 1750, 1440, 1170.

NMR (90 MHz, CDCl$_3$) $\delta$: 2.40–3.00 (4H, m), 2.67 (3H, s), 7.30–7.75 (5H, m).

EXAMPLE 38

Preparation of benzyl 2-(4-methoxyphenyl)thio-5-oxo-2-tetrahydrofurancarboxylate [Compound (38)]

MP: 105°–106° C.

IR $\nu$max (KBr)cm$^{-1}$: 1785, 1775, 1725, 1585, 1490l, 1240.

NMR (90 MHz, CDCl$_3$) $\delta$: 2.25–2.90 (4H, m), 3.77 (3H, s), 5.07 (2H, s), 6.67–7.50 (9H, m).

EXAMPLE 39

Preparation of benzyl 2-(2-thienylmethyl)thio-5-oxo-2-tetrahydrofurancarboxylate [Compound (39)]

MP: 55° C.

IR $\nu$max (KBr)cm$^{-1}$: 1780, 1730, 1245, 1175, 1050.

NMR (90 MHz, CDCl$_3$) $\delta$: 2.20–2.90 (4H, m), 4.13 (2H, s), 5.17 (2H, s), 6.87–7.30 (3H, m), 7.40 (5H, s).

EXAMPLE 40

Preparation of benzyl 2-cyclohexylthio-5-oxo-2-tetrahydrofurancarboxylate [Compound (40)]

MP: 65°–67° C.

IR $\nu$max (KBr)cm$^{-1}$: 1790, 1730, 1160.

NMR (90 MHz, CDCl$_3$) $\delta$: 0.90–1.90 (11H, m), 2.20–3.30 (4H, m), 5.27 (2H, s), 7.40 (5H, s).

EXAMPLE 41

Preparation of benzyl 2-(4-methylphenyl)thio-5-oxo-2-tetrahydrofurancarboxylate [Compound (41)]

MP: 45°–46° C.

IR $\nu$max (KBr)cm$^{-1}$: 1790, 1720, 1160, 1025, 880.

NMR (90 MHz, CDCl$_3$) $\delta$: 2.30 (3H, s), 2.37–2.90 (4H, m), 5.04 L (2H, s), 6.80–7.50 (9H, m).

EXAMPLE 42

Preparation of benzyl 2-(3-methylphenyl)thio-5-oxo-2-tetrahydrofurancarboxylate [Compound (42)]

MP: 34°–35° C.

IR $\nu$max (KBr)cm$^{-1}$: 1790, 1745, 1260, 1170, 1035.

NMR (90 MHz, CDCl$_3$) $\delta$: 2.26 (3H, s), 2.30–2.90 (4H, m), 5.02 (2H, s), 7.00–7.47 (9H, m).

EXAMPLE 43

Preparation of benzyl 2-(2-methylphenyl)thio-5-oxo-2-tetrahydrofurancarboxylate [Compound (43)]

MP: 58°–60° C.

IR $\nu$max (KBr)cm$^{-1}$: 1805, 1790, 1760, 1245, 1170, 1060, 1040.

NMR (90 MHz, CDCl$_3$) $\delta$: 2.23–3.00 (7H, m), 4.99 (2H, s), 6.90–7.60 (9H, m).

EXAMPLE 44

Preparation of benzyl 2-(2-acetylaminoethyl)thio-5-oxo-2-tetrahydrofurancarboxylate [Compound (44)]

IR $\nu$max (Neat)cm$^{-1}$: 1800, 1750, 1660, 1550, 1270, 1175.

NMR (90 MHz, CDCl$_3$) $\delta$: 1.93 (3H, s), 2.20–2.90 (6H, m), 3.20–3.50 (2H, m), 5.27 (2H, s), 5.93 (1H, bs), 7.40 (5H, s).

EXAMPLE 45

Preparation of benzyl 2-ethylthio-5-oxo-2-tetrahydrofurancarboxylate [Compound (45)]

IR $\nu$max (Neat)cm$^{-1}$: 1800, 1740, 1260, 1170, 1060.

NMR (90 MHz, CDCl$_3$) $\delta$: 1.17 (3H, t, J=7.5 Hz), 2.17–2.93 (6H, m), 5.30 (2H, s), 7.41 (5H, s).

EXAMPLE 46

Preparation of benzyl 2-(2-furylmethyl)thio-5-oxo-2-tetrahydrofurancarboxylate [Compound (46)]

MP: 60°–61° C.

IR $\nu$max (KBr)cm$^{-1}$: 1790, 1750, 1740, 1260, 1170, 1060.

NMR (90 MHz, CDCl$_3$) δ: 2.20–2.90 (4H, m), 3.97 (2H, s), 5.17 (2H, s), 6.10–6.37 (2H, m), 7.23–7.43 (6H, m).

EXAMPLE 47

Preparation of benzyl 2-(1-methyl-2-imidazolyl)thio-5-oxo-2-tetrahydrofurancarboxylate [Compound (47)]

MP: 110°–112° C.
IR νmax (KBr)cm$^{-1}$: 1800, 1750, 1400, 1270, 1150, 1060.
NMR (90 MHz, CDCl$_3$) δ: 2.30–3.25 (3H, m), 3.50–3.90 (1H, m), 3.56 (3H, s), 5.22 (2H, ABq, J=3.0, 12.0 Hz), 6.69 (1H, d, J=2.4 Hz), 6.92 (1H, d, J=2.4 Hz), 7.30 (5H, s).

EXAMPLE 48

Preparation of benzyl 2-phenylsulfonyl-5-oxo-2-tetrahydrofurancarboxylate [Compound (48)]

Compound (5) was reacted in a similar way to Example 5 to yield the title compound (48).
MP: 161°–163° C.
IR νmax (KBr)cm$^{-1}$: 1810, 1750, 1325, 1315, 1150, 1080.
NMR (90 MHz, CDCl$_3$) δ: 2.50–3.50 (4H, m), 5.10 (2H, s), 7.15–7.85 (10H, m).

EXAMPLE 49

Preparation of 2-phenylthio-5-oxo-2-tetrahydrofurancarboxylic acid [Compound (49)]

Compound (6) was reacted in a similar way to Example 11 to yield the title compound (49).
MP: 120°–121° C.
IR νmax (KBr)cm$^{-1}$: 1750, 1230, 1185, 1050, 980–1000, 755.
NMR (90 MHz, CDCl$_3$) δ: 2.30–3.00 (4H, m), 6.30–6.60 (1H, bs), 7.25–7.70 (5H, m).

EXAMPLE 50

Preparation of 2-phenylsulfonyl-5-oxo-2-tetrahydrofurancarboxylic acid [Compound (50)]

Compound (24) was reacted in a similar way to Example 11 to yield the title compound (50).
MP: 160°–161° C.
IR νmax (KBr)cm$^{-1}$: 1820, 1740, 1310, 1150, 1100.
NMR (90 MHz, CDCl$_3$) δ: 2.50–3.50 (4H, m), 7.45–8.20 (5H, m).

EXAMPLE 51

Preparation of pyrrolidinamide of 2-phenylsulfonyl-5-oxo-2-tetrahydrofurancarboxylic aicd [Compound (51)]

Thiophenol (0.20 mg), 337 mg of 5-pyrrolidinyl-4,5-dioxopentanoic acid and 348 mg of DCC were dissolved in 5 ml of dichloromethane and stirred for overnight at room temperature. The precipitated crystals were filtered off and the filtrate was concentrated. The residue was subjected to silica gel column chromatography eluting with hexane-ethyl acetate (3:1) to obtain 268 mg of the title compound (51).
IR νmax (Neat)cm$^{-1}$: 1790, 1710, 1640, 1440, 1025.
NMR (90 MHz, CDCl$_3$) δ: 1.70–2.20 (4H, m), 2.85–3.35 (4H, m), 3.35–3.75 (4H, m), 7.41 (5H, s).

EXAMPLE 52

Preparation of methyl 2-(4-pyridyl)thio-5-oxo-2-tetrahydrofurancarboxylate [Compound (52)]

To 5 ml of DMF were added 1.11 g of 4-pyridinethiol and then 0.40 g of 60% sodium hydride in a stream of argon, followed by stirring for 30 minutes at room temperature to make the thiolate solution.

Methyl 2-chloro-5-oxo-2-tetrahydrofurancarboxylate (1.79 g) was dissolved in 20 ml of tetrahydrofuran and cooled to −70° C. in a stream of argon, to which the above mentioned thiolate solution was little by little added and stirred for 30 minutes at −70° to −60° C. and then for an hour outside cooling bath. The reaction mixture after adding a small piece of dry ice was concentrated and partitioned with 200 ml of ethyl acetate and 100 ml of saturated sodium chloride. The organic phase was washed with saturated sodium chloride, dried on anhydrous magnesium sulfate and distilled under reduced pressure to remove the solvent. The residue was subjected to silica gel column chromatography eluting with ethyl acetate to obtain 3.2 g of the title compound (52).
MP: 93°–94° C.
IR νmax (KBr)cm$^{-1}$: 1785, 1750, 1570, 1485, 1440, 1415.
NMR (90 MHz, CDCl$_3$) δ: 2.3–3.0 (4H, m), 3.65 (3H, s), 7.43 and 7.57 (2H×2, each d, J=6 Hz).

EXAMPLE 53

Preparation of methyl 2-(4-pyridyl)methylthio-5-oxo-2-tetrahydrofurancarboxylate [Compound (53)]

The title compound (53) was obtained from 4-pyridylmethanethiol by a similar method to Example 52.
MP: 70°–72° C.
IR νmax (KBr)cm$^{-1}$: 1780, 1730, 1595, 1435, 1415.
NMR (90 MHz, DMSO-d$_6$) δ: 2.2–3.0 (4H, m), 3.60 (3H, s), 3.96 (2H, s), 7.33 and 8.43 (2H×2, each d, J=6 Hz).

EXAMPLE 54

Preparation of methyl 2-(4-pyridyl)methoxy-5-oxo-2-tetrahydrofurancarboxylate [Compound (54)]

4-Hydroxymethylpyridine (3.3 g), 4.8 g of 1-methyl 2-oxoglutarate and 6.2 g of DCC were dissolved in 90 ml of dichloromethane and stirred for 16 hours at room temperature. After filtering insoluble materials off, the filtrate was concentrated and subjected to silica gel column chromatography using an element of ethyl acetate to obtain 3.4 g of the title compound (54).
IR νmax (KBr)cm$^{-1}$: 1795, 1730, 1600, 1560, 1440, 1420.
NMR (90 MHz, DMSO-d$_6$) δ: 3.80 (3H, s), 4.70 (2H, s), 7.35 and 8.59 (2H×2, each d, J=6 Hz).

EXAMPLE 55

Preparation of
7-[2-(2-amino-4-thiazolyl)-(Z)-2-methox-
yiminoacetamido]-3-[4-(2-methoxycarbonyl-5-oxo-2-
tetrahydrofuranyl)thiopyridiniomethyl)]-3-cephem-4-
carboxylate [Compound (55)]

A mixture of 2.0 g of 7-[2-(2-amino-4-thiazolyl)-(Z)-2-methoxyiminoacetamido]-3-(3-oxobutyryloxy)methyl-3-cephem-4-carboxylic acid, 1.0 g of Compound (52) and 8.0 g of potassium iodide in 20 ml of 50% acetonitrile was stirred for 90 minutes at 70° C. After cooling, the reaction mixture was subjected to silica gel column chromatography using an eluent of aqueous acetone. The eluted solution was concentrated and subjected to column chromatography using Diaion CHP-20P (from Mitsubishi Chemical Industries Ltd.) and eluting with aqueous ethanol. The eluted solution was again concentrated and subjected to column chromatography using Sephadex LH-20 (from Pharmacia) and eluting with water. The resultant solution was concentrated, and lyophilized to give 16 mg of the title compound (55).

NMR (90 MHz, $D_2O:CD_3CN=1:1$) δ: 2.5–3.2 (4H, m), 3.06 and 3.60 (2H, ABq, J=18 Hz), 3.83 (3H, s), 3.93 (3H, s), 5.20 (1H, d, J=5 Hz), 5.10 and 5.59 (2H, ABq, J=14 Hz), 5.82 (1H, d, J=5 Hz), 6.90 (1H, s), 8.00 and 8.86 (2H×2, each d, J=6 Hz).

EXAMPLE 56

Preparation of
7-[2-(2-amino-4-thiazolyl)-(Z)-2-methox-
yiminoacetamido]-3-[4-(2-methoxycarbonyl-5-oxo-2-
tetrahydrofuranyl)thiomethylpyridiniomethyl-3-ceph-
em-4-carboxylate [Compound (56)]

A mixture of 413 mg of 7-[2-(2-amino-4-thiazolyl)-(Z)-2-methoxyiminoacetamido]-3-hydroxymethyl-3-cephem-4-carboxylic acid, 237 μl of tributylamine and 535 mg of Compound (53) in 10 ml of DMF was cooled to −50° C., to which 600 mg of O-phenylenephosphate was added and stirred for 10 minutes at the same temperature. After taking off the cooling bath, the mixture was further stirred for an hour under elevating to room temperature. After adding 100 ml of ethyl ether, the mixture was stirred and then the upper layer was removed by decantation. The remaining part was dissolved in 10 ml of 50% aqueous acetonitrile. The solution was subjected to column chromatography using silica gel and eluting with aqueous acetone and the eluted solution after concentration was subjected to column chromatography using Diaion CHP-20P. The eluted solution was concentrated and lyophilized to obtain 149 mg of the title compound (56).

IR νmax (KBr)cm$^{-1}$: 1770, 1740, 1615, 1520, 1390, 1270.

NMR (90 MHz, $D_2O:CD_3CN=1:1$) δ: 2.3–3.1 (4H, m), 3.10 and 3.67 (2H, ABq, J=18 Hz), 3.83 (3H, s), 4.03 (3H, s), 5.27 (1H, d, J=5 Hz), 5.25 and 5.70 (2H, ABq, J=14 Hz), 5.89 (1H, d, J=5 Hz). 6.98 (1H, s), 8.13 and 9.03 (2H×2, each d, J=18 Hz).

EXAMPLE 57

Preparation of
7-[2-(2-amino-4-thiazolyl)-(Z)-2-methox-
yiminoacetamido]-3-[4-(2-methoxycarbonyl-5-oxo-2-
tetrahydrofuranyl)oxymethylpyridiniomethyl]-3-ceph-
em-4-carboxylate [Compound (57)]

The title compound (57) was obtained from Compound (54) by a similar method to Example 56.

IR νmax (KBr)cm$^{-1}$: 1780 (sh), 1760, 1720, 1620, 1530, 1360.

NMR (100 MHz, $D_2O:CD_3CN=1:1$) δ: 2.2–3.0 (4H, m), 2.93–3.47 (2H, ABq, J=18 Hz), 3.75 (3H, s), 3.85 (3H, s), 4.92 (2H, s), 5.08 (1H, s, J=5 Hz), 5.10 and 5.50 (2H, ABq, J=14 Hz), 5.68 (1H, d, J=5 Hz), 6.75 (1H, s), 7.90 and 8.86 (2H×2, each d, J=6 Hz).

EXAMPLE 58

Preparation of methyl
2-(1-methyl-4-pyridinio)methyl-5-oxo-2-tetrahy-
drofurancarboxylate iodide [Compound (58)]

To a solution of 1.0 g of Compound (53) in 1 ml of DMF was added 1 ml of methyl iodide, followed by stirring for an hour at room temperature. The reaction mixture after adding 50 ml of ethyl ether was stirred and allowed to stand. The lower layer after adding 50 ml of ethyl acetate was treated in a similar way to above. The title compound (58), (1.38 g) was obtained upon crystallization from acetone.

MP: 135°–138° C. (decomp.)

IR νmax (KBr)cm$^{-1}$: 1770, 1730, 1630, 1560, 1500, 1450, 1430, 1380, 1260.

NMR (90 MHz, DMSO-$d_6$) δ: 2.0–3.0 (4H, m), 3.67 (3H, s), 4.30 (2H, s), 4.38 (3H, s), 8.09 and 9.00 (2H×2, each d, J=6 Hz).

EXAMPLE 59

Preparation of methyl
2-(1-benzyl-4-pyridinio)methylthio-5-oxo-2-tetrahy-
drofuran carboxylate bromide [Compound (59)]

Using benzyl bromide, Compound (53) was reacted in a similar way to Example 58 to afford the title compound (59).

MP: 68°–70° C.

IR νmax (KBr)cm$^{-1}$: 1780, 1700, 1630, 1450.

NMR (90 MHz, DMSO-$d_6$) δ: 2.0–3.2 (4H, m), 3.72 (3H, s), 4.30 (2H, s), 5.90 (2H, s), 7.46 (5H, br), 8.13 and 9.24 (2H×2, each d, J=6 Hz).

EXAMPLE 60

Preparation of methyl
2-(1-t-butoxycarbonylmethyl-4-pyridinio)methylthio-5-
oxo-2-tetrahydrofurancarboxylate bromide [Compound (60)]

Using t-butyl 2-bromoacetate, Compound (53) was reacted in a similar way to Example 58 to afford the title compound (60).

IR νmax (Neat)cm$^{-1}$: 1780, 1730, 1635, 1460, 1240.

NMR (90 MHz, DMSO-$d_6$) δ: 1.55 (9H, s), 2.1–3.2 (4H, m), 3.80 (3H, s), 4.53 (2H, s), 5.88 (2H, s), 8.61 and 9.50 (2H×2, each d, J=6 Hz).

EXAMPLE 61

Preparation of methyl 2-(1-carboxymethyl-4-pyridinio)methylthio-5-oxo-2-tetrahydrofurancarboxylate bromide [Compound (61)]

A mixture of 1.0 g of Compound (60) in 10 ml of trifluoroacetic acid was stirred for 2 hours at room temperature. The reaction mixture was concentrated and pulverized by addition of ethyl ether to obtain 0.84 g of the title compound (61).

IR $\nu$max (KBr)cm$^{-1}$: 1770, 1700, 1640, 1465.

NMR (90 MHz, DMSO-d$_6$) $\delta$: 2.2–3.2 (4H, m), 3.62 (3H, s), 4.35 (2H, s), 5.60 (2H, s), 8.20 and 9.05 (2H×2, each d, J=6 Hz).

EXAMPLE 62

Preparation of methyl 2-(1-methyl-4-pyridinio)thio-5-oxo-2-tetrahydrofurancarboxylate iodide [Compound (62)]

Compound (52) was reacted in a similar way to Example 58 to afford the title compound (62).

MP: 140°–145° C. (decomp.)

IR $\nu$max (KBr)cm$^{-1}$: 1785, 1740, 1620, 1550, 1490, 1450, 1340, 1280, 1260.

NMR (90 MHz, DMSO-d$_6$) $\delta$: 2.4–3.4 (4H, m), 3.79 (3H, s), 4.28 (3H, s), 8.01 and 8.86 (2H×2, each d, J=6 Hz).

EXAMPLE 63

Preparation of 4-nitrobenzyl 2-(1-methyl-4-pyridinio)thio-5-oxo-2-tetrahydrofurancarboxylate iodide [Compound (63)]

Compound (14) was reacted in a similar way to Example 58 to afford the title compound (63).

IR $\nu$max (Neat)cm$^{-1}$: 1790, 1740, 1625, 1490, 1450, 1345, 1260.

NMR (90 MHz, DMSO-d$_6$) $\delta$: 2.1–3.2 (4H, m), 4.16 (3H, s), 5.40 (2H, s), 7.59 and 8.20 (2H×2, each d, J=9 Hz), 8.01 and 8.86 (2H×2, each d, J=6 Hz).

EXAMPLE 64

Preparation of 4-nitrobenzyl 2-(1-methyl-4-pyridinio)methylthio-5-oxo-2-tetrahydrofurancarboxylate iodide [Compound (64)]

Compound (16) was reacted in a similar way to Example 58 to afford the title compound (64).

IR $\nu$max (Neat)cm$^{-1}$: 1780, 1730, 1630, 1500, 1340, 1260.

NMR (90 MHz, DMSO-d$_6$) $\delta$: 2.1–3.1 (4H, m), 4.30 (2H, s), 4.34 (3H, s), 5.31 (2H, s), 7.66 and 8.25 (2H×2, each, J=9 Hz), 8.03 and 8.91 (2H×2, each d, J=6 Hz).

EXAMPLE 65

Preparation of 4-nitrobenzyl 2-(1methyl-2-pyridinio)methylthio-5-oxo-2-tetrahydrofurancarboxylate iodide [Compound (65)]

Compound (12) was reacted in a similar way to Example 58 to afford the title compound (65).

IR $\nu$max (Neat)cm$^{-1}$: 1780, 1620, 1500, 1450, 1340.

NMR (90 MHz, DMSO-d$_6$) $\delta$: 2.1–3.4 (4H, m), 4.66 (3H, s), 5.66 (2H, s), 7.8–9.7 (8H, m).

EXAMPLE 66

Preparation of 2-(1-methyl-4-pyridinio(methylthio-5-oxo-2-tetrahydrofurancarboxylate [Compound (66)]

Compound (64), (200 mg) was dissolved in a mixed solvent of 5 ml of tetrahydrofuran and 10 ml of water, to which 200 mg of 10% palladium-carbon was added. The mixture was stirred for 3 hours at room temperature in a stream of hydrogen. The reaction mixture was filtered to remove insoluble materials. The filtrate was concentrated and subjected to column chromatography using Diaion CHP-20P and eluting with water. The eluate was concentrated and lyophilized to obtain 56 mg of the title compound (66).

IR $\nu$max (Neat)cm$^{-1}$: 1760, 1630, 1360, 1300, 1240.

NMR (90 MHz, D$_2$O:CD$_3$CN=1:1) $\delta$: 2.1–3.3 (4H, m), 4.33 (2H, s), 4.50 (3H, s), 8.19 and 8.91 (2H×2, each d, J=6 Hz).

What we claim is:

1. A compound of the formula

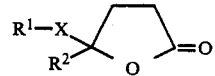

wherein R$^1$ is (1) C$_{1-6}$alkyl which is unsubstituted or is substituted by pyridyl, thienyl, furyl or phenyl, (2) C$_{4-6}$cycloalkyl, (3) phenyl which is unsubstituted or is substituted by halogen, nitro, cyano, C$_{1-3}$ or C$_{1-3}$ alkoxyl, (4) pyridyl which is unquaternized or quaternized and which is unsubstituted or is substituted by methyl, or (5) imidazolyl which is unsubstituted or is substituted by methyl; R$^2$ is a carboxyl group which is free or is esterified by C$_{1-10}$alkyl, benzyl, nitrobenzyl or benzhydryl; and X is an oxygen atom or a sulfur atom which is unoxidized or is oxidized, or a salt thereof.

2. A compound according to claim 1 in which R$^1$ is 2-pyridylmethyl, 4-pyridylmethyl, 2-pyridyl, 4-pyridyl, 4-chlorophenyl, phenyl or 4-nitrobenzyl; R$^2$ is a carboxyl group which is free or is esterified by benzyl, nitrobenzyl, benzyhydryl or C$_{1-10}$alkyl; and X is —O—, —S—, —SO— or —SO$_2$, or a salt thereof.

3. A compound of claim 1 in which R$^1$ is 2-pyridyl or 4-pyridyl which is unquaternized or is quaternized with C$_{1-3}$alkyl and halogen.

4. A compound of claim 1 in which X is sulfur atom.

5. A compound of claim 1 in which is benzyl 2-phenylthio-5-oxo-2-tetrahydrofurancarboxylate, methyl 2-phenylthio-5-oxo-2-tetrahydrofurancarboxylate or benzyl 2-(4-chlorophenyl)thio-5-oxo-2-tetrahydrofurancarboxylate.

* * * * *